(12) United States Patent
You et al.

(10) Patent No.: US 9,188,662 B2
(45) Date of Patent: Nov. 17, 2015

(54) BEAM SPLITTER FOR 3D CAMERA, AND 3D IMAGE ACQUISITION APPARATUS EMPLOYING THE BEAM SPLITTER

(75) Inventors: Jang-woo You, Yongin-si (KR); Yong-hwa Park, Yongin-si (KR); Yong-chul Cho, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 546 days.

(21) Appl. No.: 13/162,224

(22) Filed: Jun. 16, 2011

(65) Prior Publication Data

US 2012/0105594 A1    May 3, 2012

(30) Foreign Application Priority Data

Oct. 29, 2010    (KR) .................. 10-2010-0107012

(51) Int. Cl.
| | |
|---|---|
| *G02B 27/14* | (2006.01) |
| *H04N 13/02* | (2006.01) |
| *G01S 7/481* | (2006.01) |
| *G01S 17/89* | (2006.01) |
| *H04N 5/225* | (2006.01) |
| *H04N 5/33* | (2006.01) |
| *G02B 27/10* | (2006.01) |

(Continued)

(52) U.S. Cl.
CPC ............... *G01S 7/4811* (2013.01); *G01S 17/89* (2013.01); *G02B 27/1013* (2013.01); *G02B 27/141* (2013.01); *H04N 5/2254* (2013.01); *H04N 5/33* (2013.01); *G03B 15/03* (2013.01); *G03B 35/08* (2013.01)

(58) Field of Classification Search
None
See application file for complete search history.

(56) References Cited

U.S. PATENT DOCUMENTS

| | | | | |
|---|---|---|---|---|
| 3,446,560 | A * | 5/1969 | Brasier | 356/146 |
| 4,468,119 | A * | 8/1984 | Hamar | 356/152.1 |
| 7,640,691 | B2 * | 1/2010 | Karcher et al. | 42/118 |

(Continued)

FOREIGN PATENT DOCUMENTS

| | | |
|---|---|---|
| EP | 2221655 A1 | 8/2010 |
| JP | 9-184907 A | 7/1997 |

(Continued)

OTHER PUBLICATIONS

Jack, Keith, and Vladimir Tsatsulin. Dictionary of Video and Television Technology. Amsterdam: Newnes, 2002. Print.*

(Continued)

*Primary Examiner* — Christopher S Kelley
*Assistant Examiner* — Kaitlin A Retallick
(74) *Attorney, Agent, or Firm* — Sughrue Mion, PLLC

(57) ABSTRACT

A beam splitter and a 3D image acquisition apparatus including the beam splitter are provided. The beam splitter includes a light incident surface on which light having a first wavelength and light having a second wavelength are incident; a beam splitting surface which is inclined to the light incident surface and reflects the light having the first wavelength and transmits the light having the second wavelength; a first light exit surface through which the light having the first wavelength reflected from the beam splitting surface exits; a first reflective surface which reflects the light having the second wavelength transmitted by the beam splitting surface; a second reflective surface which reflects the light having the second wavelength reflected from the first reflective surface; and a second light exit surface through which the light having the second wavelength reflected from the second reflective surface exits.

21 Claims, 10 Drawing Sheets

(51) Int. Cl.
  *G03B 15/03* (2006.01)
  *G03B 35/08* (2006.01)

(56) References Cited

U.S. PATENT DOCUMENTS

| | | | |
|---|---|---|---|
| 2004/0263790 A1* | 12/2004 | VanOverloop et al. | 353/31 |
| 2006/0221250 A1* | 10/2006 | Rossbach et al. | 348/630 |
| 2007/0201342 A1 | 8/2007 | Molitor et al. | |
| 2010/0109980 A1* | 5/2010 | Tohara et al. | 345/32 |
| 2010/0128109 A1* | 5/2010 | Banks | 348/46 |
| 2011/0228260 A1* | 9/2011 | Yablon | 356/73.1 |

FOREIGN PATENT DOCUMENTS

| | | |
|---|---|---|
| JP | 9-281441 A | 10/1997 |
| JP | 10-341449 A | 12/1998 |
| JP | 2006337286 A | 12/2006 |
| JP | 2008249430 A | 10/2008 |
| KR | 2002-0078509 A | 10/2002 |

OTHER PUBLICATIONS

Communication Issued Apr. 27, 2012, by the Intellectual Property Office of Europe in counterpart European Application No. 11181234.3-1234.

* cited by examiner

BEAM SPLITTER FOR 3D CAMERA, AND 3D IMAGE ACQUISITION APPARATUS EMPLOYING THE BEAM SPLITTER

CROSS-REFERENCE TO RELATED APPLICATIONS

This application claims priority under 35 U.S.C. §119(a) from Korean Patent Application No. 10-2010-0107012, filed on Oct. 29, 2010, in the Korean Intellectual Property Office, the disclosure of which is incorporated herein in its entirety by reference.

BACKGROUND

1. Field

The present disclosure relates to a beam splitter for a 3D camera, and a 3D image acquisition apparatus such as a 3D camera, wherein the beam splitter is capable of separating a color image and a depth image, which are incident via a same incident surface, to proceed along different paths, and wherein the 3D image acquisition apparatus is capable of simultaneously capturing a color image and a depth image by using one lens and the beam splitter.

2. Description of the Related Art

Due to the development and increase in use of 3D display apparatuses, the development of 3D content has become important. Thus, research has been conducted into providing a 3D camera which allows a user to directly produce 3D content. A 3D camera may also be referred to as a RGBD image camera since it requires not only typical two-dimensional (2D) RGB color image information but also depth information (D).

The depth information is information about a distance between the 3D camera and surfaces of an object, and may be obtained by using a stereo vision method involving the use of two cameras, or by using a triangulation method involving structured light and a camera. However, according to the aforementioned methods, the accuracy of the distance information deteriorates as the distance between the 3D camera and the object becomes great. Also, it is difficult to obtain accurate distance information using the aforementioned methods because they are dependent upon a status of the surfaces of the object in question.

In order to solve this problem, a Time-of-Flight (TOF) technique has been introduced. The TOF technique irradiates a laser beam to an object, and then measures a travel time of the laser beam that is reflected from the object and is received by a light receiving unit. According to the TOF technique, light having a particular wavelength (e.g., near infrared rays having a wavelength of about 850 nm) is irradiated to the object by using a light emitting diode (LED) or a laser diode (LD), a light receiving unit receives the light that has the same wavelength and is reflected from the object, and a processing procedure is performed so as to extract depth information by modulating the received light using a modulator having a known gain wavelength. Various TOF techniques are available using various processing procedures.

A 3D camera used in conjunction with a TOF technique includes an optical system structure enabling it to simultaneously acquire a color image including general image information, and a depth image including depth information. For example, the 3D camera may respectively capture the color image and the depth image by using separate optical modules. However, in such a case, a mismatch may occur between the color image and the depth image due to a mismatch between an optical axis of an optical system used to obtain the color image, and an optical axis of an optical system used to obtain the depth image. Also, such a setup requires two object lenses in order to separately capture the color image and the depth image.

In this regard, in order to secure a match between a color image and a depth image and to simultaneously capture the color image and the depth image by using one object lens, an optical system structure in which a color image and a depth image may share one object lens is proposed. For example, in a color/depth image shared-type optical system, a color image and a depth image that are provided via a single object lens may be split by using a beam splitter, and the separate color image and depth image may be captured using separate image sensors, respectively. Thus, a/depth image shared-type optical system may have one object lens, one beam splitter, and two image sensors. A 3D camera employing this optical system structure may secure a match between two images, thereby acquiring a high-quality 3D image and achieving an excellent result with respect to form.

In order to extract distance information by using a TOF technique, it is necessary to arrange a modulator so as to modulate light that is reflected from the object. The modulator may be broadly classified as a reflection-type modulator or a transmittance-type modulator. Reflection-type modulators are more easily embodied are more frequently used. However, in a case in which a reflection-type modulator is used, a huge amount of light loss may occur in a beam splitter, and this light loss may decrease a signal-to-noise ratio (SNR) so that the light loss may deteriorate the accuracy of the depth information.

SUMMARY

The following description relates to a beam splitter capable of separating a color image and a depth image, which are incident via a same incident surface, and causing the different images to proceed along different paths.

The following description further relates to a 3D image acquisition apparatus capable of simultaneously capturing a color image and a depth image by using a single lens and a beam splitter.

According to an aspect of an exemplary embodiment, a beam splitter includes a light incident surface on which light having a first wavelength and light having a second wavelength different from the first wavelength are commonly incident; a beam splitting surface which is inclined with respect to the light incident surface, reflecting the light having the first wavelength, and transmitting the light having the second wavelength; a first light exit surface through which the light having the first wavelength that has been reflected from the beam splitting surface exits the beam splitter; a first reflective surface reflecting the light having the second wavelength that has passed through the beam splitting surface; a second reflective surface reflecting the light having the second wavelength that has been reflected from the first reflective surface; and a second light exit surface through which the light having the second wavelength that has been reflected from the second reflective surface exits the beam splitter.

The light incident surface, the first light exit surface, and the second light exit surface may be perpendicular to optical axes of light respectively passing through the light incident surface, the first light exit surface, and the second light exit surface.

The second light exit surface may be adjacent to the light incident surface, the first light exit surface, and the first reflective surface and may face the second reflective surface.

The beam splitter may further include a first reflective member disposed on the first reflective surface, and a second reflective member disposed on the second reflective surface.

One of the first reflective member and the second reflective member may include a reflection-type modulator for modulating and reflecting the light having the second wavelength, and the other one of the first reflective member and the second reflective member may include a reflective mirror.

The first reflective surface may be inclined toward the second reflective surface, and the second reflective surface may be inclined toward the second light exit surface.

The one of the first reflective surface and the second reflective surface whereon the reflection-type modulator is disposed may be inclined, whereby an angle between an optical axis of the light having the second wavelength incident on the modulator and a line normal to the modulator is greater than about 0 degrees and less than about 45 degrees.

The angle between the optical axis of the light having the second wavelength incident on the reflection-type modulator and the line normal to the modulator may be about 22.5 degrees.

The beam splitter may include a first part prism adhered to a second part prism, where the first and second part prisms are polyhedral prisms.

The beam splitting surface may include a thin film coating formed on an interface between the first part prism and the second part prism.

The light incident surface and the first light exit surface may be disposed on a front surface and a side surface of the first part prism, respectively, and may be adjacent to each other, and the first reflective surface may be disposed on a rear surface of the second part prism so as to face the light incident surface.

The second reflective surface may be jointly formed by an inclined top surface of the first part prism and an inclined top surface of the second part prism, and the second light exit surface may be jointly formed by a bottom surface of the first part prism and a bottom surface of the second part prism.

The beam splitter may further include a relay lens disposed on the second light exit surface.

The beam splitter may further include a relay mirror disposed on one of the first reflective surface and the second reflective surface.

According an aspect of another exemplary embodiment, a beam splitter includes a light incident surface on which light having a first wavelength and light having a second wavelength different from the first wavelength are commonly incident; a beam splitting surface inclined with respect to the light incident surface, reflecting the light having the first wavelength, and transmitting the light having the second wavelength; a first light exit surface through which the light having the first wavelength that has been reflected from the beam splitting surface exits; a reflective surface reflecting the light having the second wavelength that has passed through the beam splitting surface; a second light exit surface through which the light having the second wavelength that has been reflected from the reflective surface exits; and a reflection-type modulator disposed on the reflective surface, and modulating and reflecting the light having the second wavelength.

The beam splitter may be formed by adhering a first part prism to a second part prism, wherein the first and second part prisms are polyhedral prisms, the beam splitting surface may include a thin film coating formed on an interface between the first part prism and the second part prism.

The light incident surface and the first light exit surface may be a front surface and a bottom surface of the first part prism, respectively, and may be adjacent to each other.

The reflective surface and the second light exit surface may be an inclined rear surface and an inclined top surface of the second part prism, respectively.

According to an aspect of another exemplary embodiment, a beam splitter includes a light incident surface on which light having a first wavelength and light having a second wavelength different from the first wavelength are commonly incident; a beam splitting surface inclined with respect to the light incident surface, transmitting the light having the first wavelength, and reflecting the light having the second wavelength; a first light exit surface through which the light having the first wavelength that has passed through the beam splitting surface exits; a reflective surface reflecting the light having the second wavelength that has been reflected from the beam splitting surface; a second light exit surface through which the other light having the second wavelength that has been reflected from the reflective surface exits; and a reflection-type modulator disposed on the reflective surface, modulating and reflecting the light having the second wavelength.

The beam splitter may be formed by adhering an inclined rear surface of a first part prism having a shape of a polyhedral prism to a second part prism having a right triangle shape, the beam splitting surface may include a thin film coating formed on an interface between the first part prism and the second part prism.

The light incident surface, the reflective surface, and the second light exit surface may be a front surface, an inclined top surface, and a bottom surface of the first part prism, respectively, and the first light exit surface may be a rear surface of the second part prism.

The light having the first wavelength may be visible light and the light having the second wavelength may be infrared light.

According to an aspect of another exemplary embodiment, a 3D image acquisition apparatus includes an infrared light source for irradiating infrared light to an object; an object lens for focusing visible light and infrared light that have been reflected from the object; a beam splitter according to one of the aforementioned exemplary beam splitters; a first image sensor for generating an image with respect to the visible light; a second image sensor for generating an image with respect to the infrared light; and a 3D image signal processor (ISP) for generating a 3D image having depth information by using the images generated by the first and second image sensors.

The beam splitter may be configured to split the visible light and the infrared light and to provide the visible light to the first image sensor and to provide the infrared light to the second image sensor.

The first image sensor may face a first light exit surface of the beam splitter, and the second image sensor may face a second light exit surface of the beam splitter.

The first image sensor may be directly disposed on the first light exit surface of the beam splitter, and the second image sensor may be directly disposed on the second light exit surface of the beam splitter.

BRIEF DESCRIPTION OF THE DRAWINGS

These and/or other aspects will become apparent and more readily appreciated from the following description of embodiments, taken in conjunction with the accompanying drawings of which.

DETAILED DESCRIPTION

Figure 1:
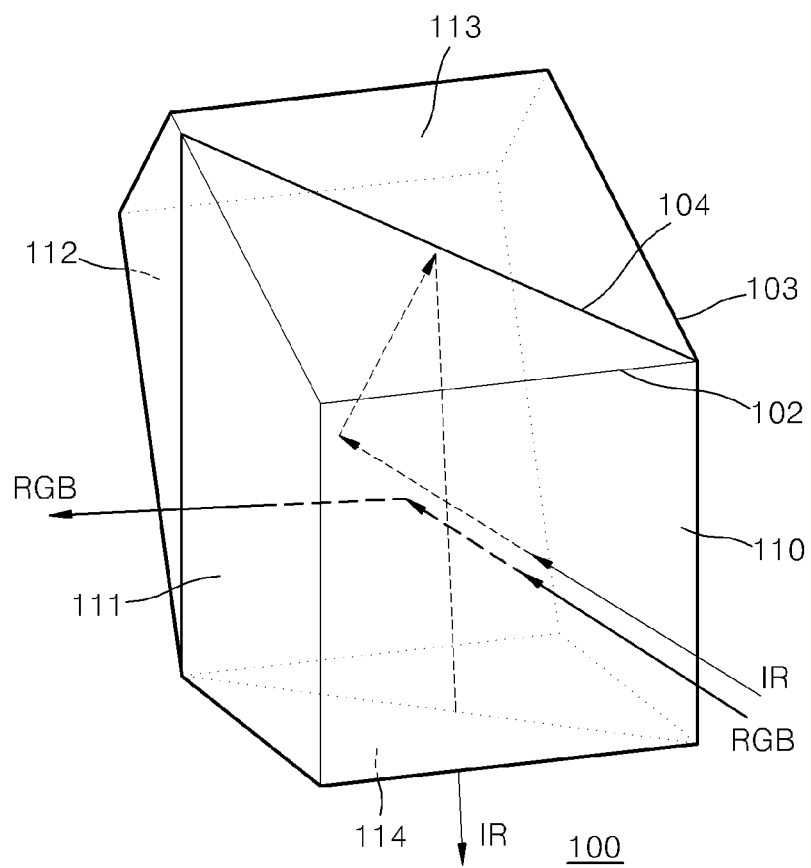
FIG. 1 is a perspective view of a beam splitter according to an embodiment.

Reference will now be made in detail to embodiments of a beam splitter for a 3D camera, and a 3D image acquisition apparatus employing the beam splitter, examples of which are illustrated in the accompanying drawings. In the drawings, like reference numerals denote like elements, and the size of each component may be exaggerated for clarity.

FIG. 1 is a perspective view of a beam splitter 100 according to an embodiment. Referring to FIG. 1, the beam splitter 100 may have the shape of a pentaprism. The pentaprism is a polyhedral prism that is formed of an optically transparent material including glass and which has a pentagon-shaped cross-section. The beam splitter 100 may be formed to have the shape of a pentaprism by adhering at least two polygonal prisms to each other. The beam splitter 100 may be formed by adhering an inclined surface of a first part prism 102 having inclined surfaces to an inclined surface of a second part prism 103 having inclined surfaces. Accordingly, the beam splitter 100 may have an inclined beam splitting surface 104 between the first part prism 102 and the second part prism 103. Here, the first part prism 102 and the second part prism 103 having polygonal shapes may be formed of the same material.

Figure 2:
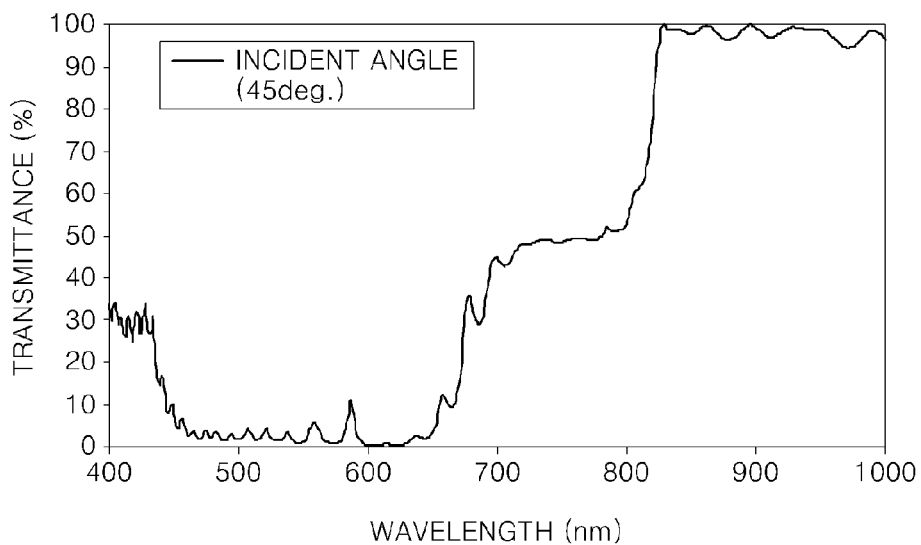
FIG. 2 is a graph illustrating a variation in a transmittance with respect to wavelength of a thin film coating formed on an interface of the beam splitter of FIG. 1.

A thin film coating 105 (refer to FIG. 5B) is disposed on the beam splitting surface 104 and the thin film coating 105 may reflect or transmit light depending on wavelength of the light. The thin film coating 105 may function as a long wavelength pass (LWP) for transmitting light having a relatively long wavelength, or may function as a short wavelength pass (SWP) for transmitting light having a relatively short wavelength. For example, the thin film coating 105 may be formed to reflect visible light and to transmit infrared light, or may be formed to transmit visible light and to reflect infrared light. FIG. 2 is a graph illustrating a variation in the transmittance with respect to wavelength of a thin film coating 105 formed to reflect visible light and to transmit infrared light. Referring to the graph of FIG. 2, the thin film coating 105 may exhibit a reflectance reaching about 100% (that is, transmittance reaching about 0%) with respect to a wavelength band from about 450 nm to about 650 nm, and may exhibit a transmittance reaching about 100% with respect to a wavelength band equal to or greater than about 800 nm.

Figure 3:
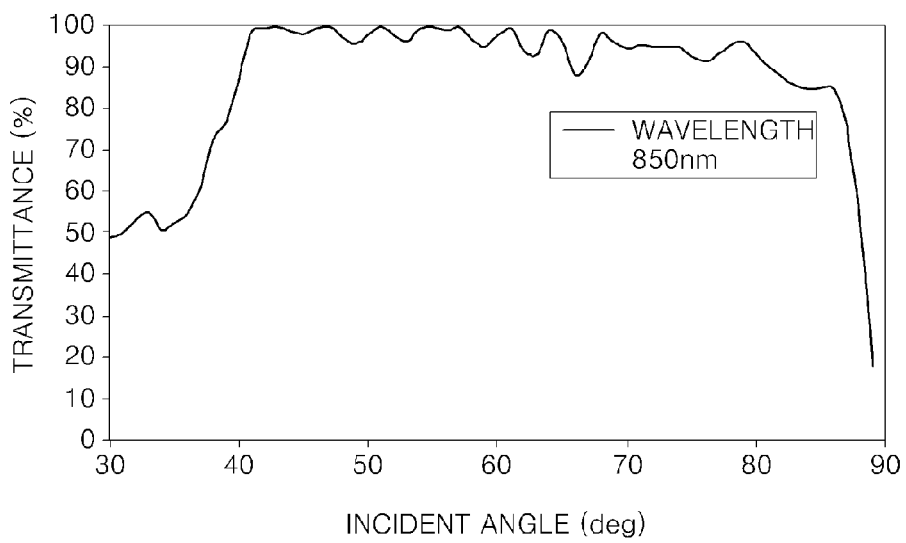
FIG. 3 is a graph illustrating variation of transmittance with respect to incident angle of a thin film coating formed on an interface of the beam splitter of FIG. 1.

Also, light incident on the beam splitter 100 might not be collimated parallel light, so that an incident angle of the light incident on the thin film coating 105 may not be consistent. Thus, the thin film coating 105 may be formed in such a manner that a transmittance or reflectance of the light incident thereon does not vary with respect to various incident angles. FIG. 3 is a graph illustrating a variation of transmittance with respect to an incident angle of the thin film coating 105 in an infrared light band. Referring to FIG. 3, the thin film coating 105 exhibits transmittance reaching about 100% with respect to an incident angle between about 40 degrees and about 80 degrees. For example, the thin film coating 105 may be formed by alternately stacking two transparent materials (e.g., $SiO_2$ and $TiO_2$) having different refractive indexes so as to have a thickness from several to several tens of nanometers. A structure of the thin film coating 105 having a desired optical characteristic may be designed using a multi-stack thin film technique as would be understood by one of skill in the art, and thus a detailed description thereof is omitted here.

Figure 4A:
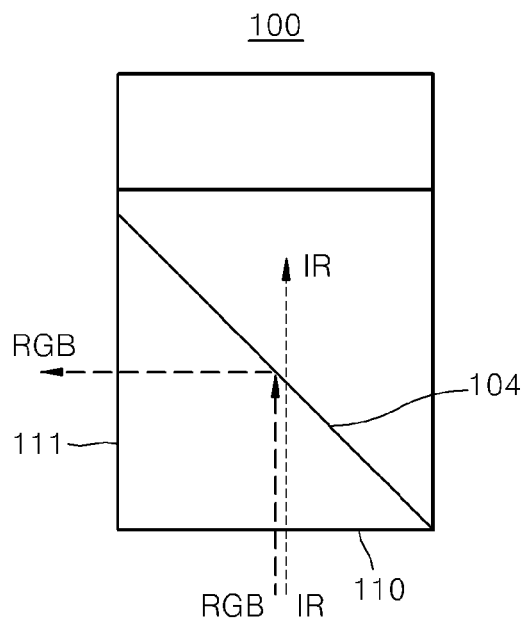
FIGS. 4A, 4B, and 4C are, respectively, a plane view, a front view, and a right side view of the beam splitter of FIG. 1.
Figure 4B:
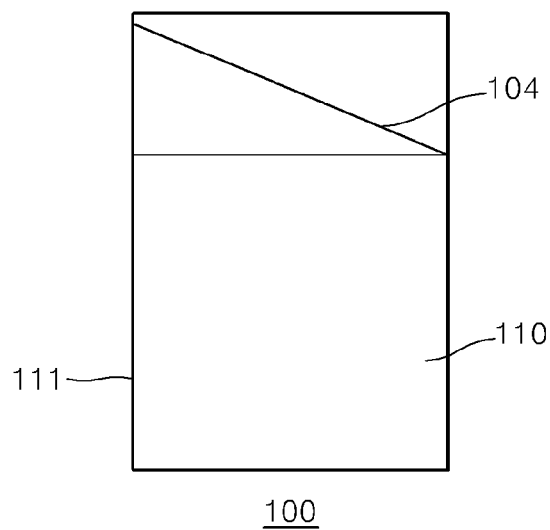
Figure 4C:
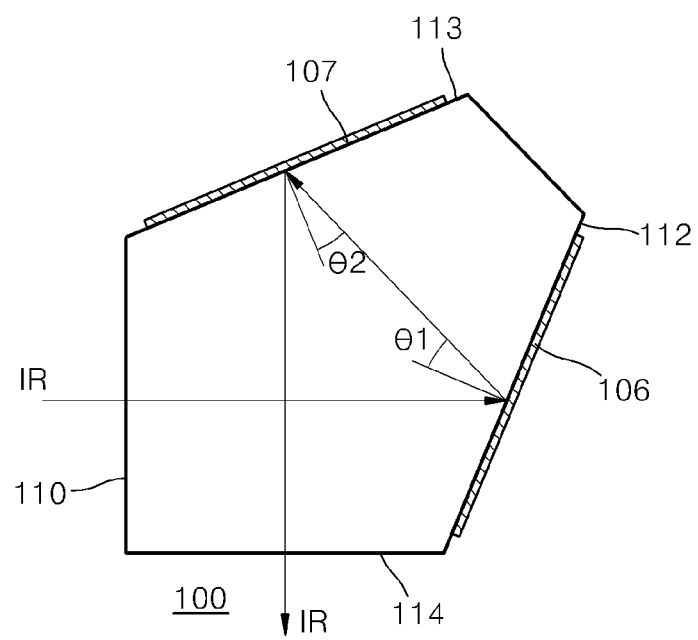

FIGS. 4A, 4B, and 4C are, respectively, a plane view, a front view, and a right side view of the beam splitter 100 when a light incident surface 110 of the beam splitter 100 is regarded as a front surface. Hereinafter, with reference to FIGS. 1, and 4A through 4C, a detailed operation and structure of the beam splitter 100 will now be described. First, incident light having two different wavelengths enters the beam splitter 100 via the light incident surface 110 of the beam splitter 100. Here, the incident light may include RGB light having a relatively short wavelength in a visible light band, and IR light having a relatively long wavelength in an infrared light band. The RGB light in the visible light band, and the IR light in the infrared light band may be simultaneously incident on the light incident surface 110. The light incident surface 110 may be perpendicular to an optical axis so as to allow the incident light to be substantially perpendicular to the light incident surface 110. Thus, the incident light may enter the beam splitter 100 without being refracted by the light incident surface 110. The light incident surface 110 may be disposed in the first part prism 102 of the beam splitter 100.

The RGB and IR light is then incident on the beam splitting surface 104 whereon the thin film coating 105 is formed. For the purposes of this description, it is assumed that the thin film coating 105 reflects the RBG light in the visible light band and transmits the IR light in the infrared light band. The RGB light is reflected from the beam splitting surface 104 and then exits the beam splitter 100 via a first light exit surface 111 that is at a left side of the beam splitter 100, as shown in FIG. 1. In order to allow the RGB light to exit the beam splitter 100 without being refracted by the first light exit surface 111, the first light exit surface 111 may be perpendicular to a travel direction of the RGB light which has been reflected by the beam splitting surface 104. The first light exit surface 111 may be adjacent to the light incident surface 110 and may be disposed in the first part prism 102. In this case, an angle between the light incident surface 110 and the first light exit surface 111 may be a right angle, and the beam splitting surface 104 may be inclined at about 45 degrees with respect to the first light exit surface 111. The light that exits the beam splitter 100 via the first light exit surface 111 may be directed to a dedicated image sensor, namely, a first image sensor 520 (refer to FIG. 6) including a charge-coupled device (CCD). A travel path of the RGB light is shown in the plane view of FIG. 4A.

The IR light is transmitted through the beam splitting surface 104 without refraction and then is incident on a first reflective surface 112 that faces the light incident surface 110. For example, the first reflective surface 112 may be disposed at a rear surface of the second part prism 103 of the beam splitter 100. A first reflective member 106 (refer to FIG. 4C) is disposed on the first reflective surface 112 so as to reflect incident light. Also, the first reflective surface 112 is inclined at a predetermined angle toward a second reflective surface 113 so as to prevent reflected IR light from returning to a previous path. Thus, the IR light which has been reflected from the first reflective surface 112, travels to the second reflective surface 113.

The second reflective surface 113 may be jointly formed by an inclined top surface of the first part prism 102 and an inclined top surface of the second part prism 103. A second reflective member 107 (refer to FIG. 4C) is disposed on the second reflective surface 113 so as to reflect incident light. Also, in order to prevent the IR light which has been reflected from the second reflective surface 113, from returning to a previous path, the second reflective surface 113 is also inclined at a predetermined angle toward a second light exit surface 114. Thus, the IR light which has been reflected from the second reflective surface 113, travels to the second light exit surface 114.

The IR light which has been reflected from the second reflective surface 113, exits the beam splitter 100 via the second light exit surface 114 disposed as a bottom surface of the beam splitter 100. The second light exit surface 114 may be jointly formed by a bottom surface of the first part prism 102 and a bottom surface of the second part prism 103. As illustrated in FIG. 1, the second light exit surface 114 may be adjacent to the light incident surface 110 of the beam splitter 100, the first light exit surface 111, and the first reflective surface 112, respectively, and may face the second reflective surface 113. Also, in order to allow the IR light to exit the beam splitter 100 without being refracted by the second light exit surface 114, the second light exit surface 114 may be perpendicular to a travel direction of the IR light which has been reflected from the second reflective surface 113. The light that exits the beam splitter 100 via the second light exit surface 114 may be directed to a dedicated image sensor, namely, a second image sensor 530 (refer to FIG. 6) which may include a CCD. A travel path of the IR light is shown in the right side view of FIG. 4C.

One of the first reflective member 106 disposed on the first reflective surface 112, and the second reflective member 107 disposed on the second reflective surface 113 may be a reflection-type modulator capable of modulating the IR light with a predetermined gain waveform, and the other one of the first reflective member 106 and the second reflective member 107 may be a simple reflective mirror. For example, the first reflective member 106 may be a reflection-type modulator and the second reflective member 107 may be a simple reflective mirror. Alternatively, the first reflective member 106 may be a simple reflective mirror and the second reflective member 107 may be a reflection-type modulator. In a case in which the first reflective member 106 is a reflection-type modulator, IR light may be modulated by the reflection-type modulator at the first reflective surface 112 and then the modulated IR light may be reflected by the second reflective surface 113. In a case in which the second reflective member 107 is a reflection-type modulator, IR light may be modulated by the reflection-type modulator at the second reflective surface 113 and then the modulated IR light may be incident on the second light exit surface 114.

In this way, a variation of an optical characteristic of the light that is modulated and reflected by the reflection-type modulator becomes great as an incident angle with respect a line normal to the reflection-type modulator increases. That is, as an inclination angle of light incident on the reflection-type modulator increases, more distortion may occur in the light that is modulated and reflected by the reflection-type modulator. Thus, a reflective surface whereon the reflection-type modulator is disposed may be disposed such that an angle between an optical axis of incident IR light and a line normal to the reflective surface of the modulator is as small as possible, e.g., within about 45 degrees. That is, if the first reflective member 106 on the first reflective surface 112 is a reflection-type modulator, an angle θ1 of FIG. 4C may be about 45 degrees or less. If the second reflective member 107 on the second reflective surface 113 is a reflection-type modulator, an angle θ2 of FIG. 4C may be less than about 45 degrees. However, when the optical axis of the incident IR light is parallel to the line normal line to the reflective surface, the IR light is reflected back along its previous path. Thus, the reflective surface on which the reflection-type modulator is disposed may be arranged such that the angle between the optical axis of the incident IR light and the line normal to its reflective surface is greater than 0 degrees. For example, an incident angle (θ1 or θ2) at which the IR light is incident on the reflection-type modulator may be greater than 0 degrees and less than about 45 degrees. The incident angle (θ1 or θ2) may be about 22.5 degrees.

Figure 5A:
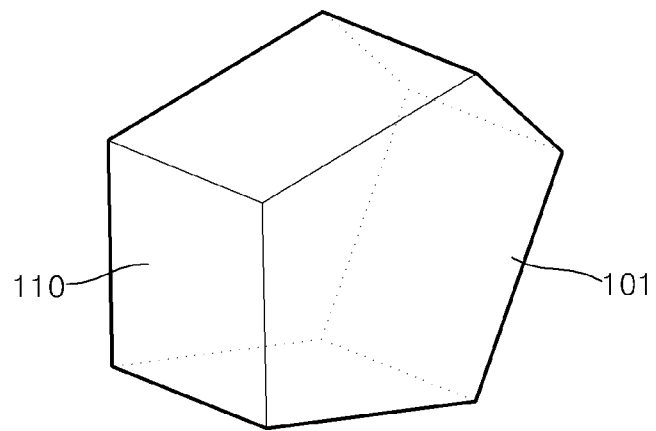
FIGS. 5A through 5D are perspective views illustrating a process of manufacturing the beam splitter of FIG. 1.
Figure 5B:
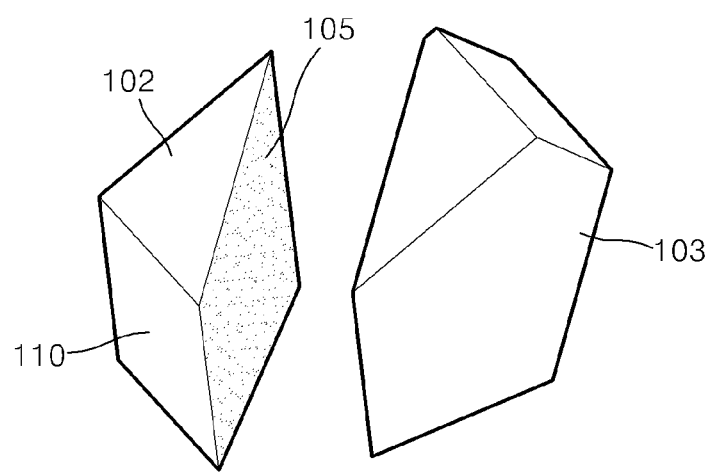
Figure 5C:
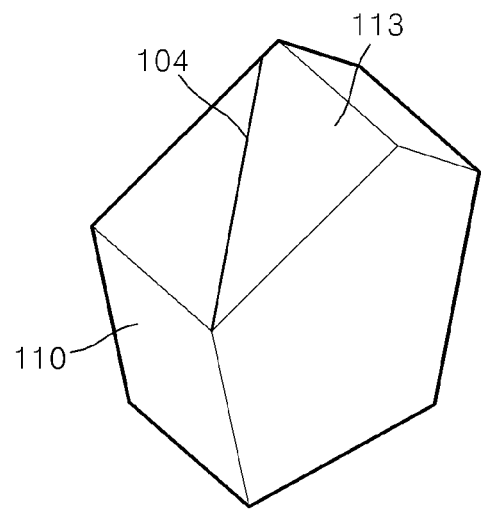
Figure 5D:
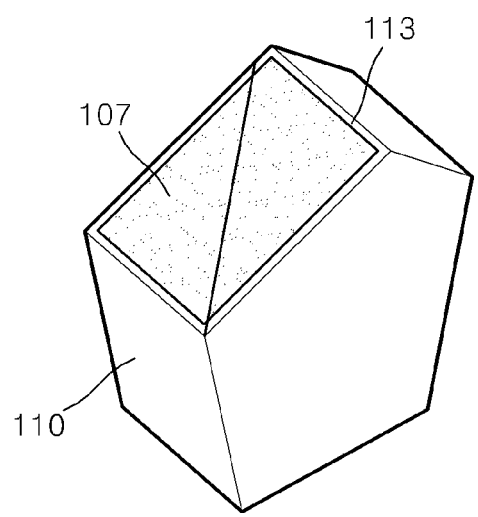

FIGS. 5A through 5D are perspective views for illustrating a process of manufacturing the beam splitter 100 so that the beam splitter 100 has a beam splitting surface 104 whereon the thin film coating 105 is formed. First, referring to FIG. 5A, an integrally-formed pentaprism 101 is provided. As illustrated in FIG. 5B, the pentaprism 101 is vertically cut at an inclination angle of about 45 degrees with respect to the light incident surface 110. Thereby, the pentaprism 101 is divided into the first part prism 102 and the second part prism 103. Cut surfaces of the first part prism 102 and the second part prism 103 are polished. A thin film coating 105 is formed on one of the cut surfaces of the first part prism 102 and the second part prism 103. Referring to FIG. 5B, the thin film coating 105 may be formed on the cut surface of the first part prism 102. As illustrated in FIG. 5C, the first part prism 102 and the second part prism 103 may be adhered again so that the thin film coating is sandwiched between the first part prism 102 and the second part prism 103. For example, a ultraviolet (UV) adhesive may be applied on the cut surfaces of the first part prism 102 and the second part prism 103, the cut surfaces may be adhered, and then the UV adhesive on the beam splitting surface 104 may be hardened using a UV beam. An exterior surface of the beam splitter 100 is polished. As illustrated in FIG. 5D, the first reflective member 106 and the second reflective member 107 may be disposed on the first reflective surface 112 and the second reflective surface 113, respectively.

The beam splitter 100 according to this embodiment may effectively separate light of two different wavelengths that is incident on the same light incident surface 110. Also, although light in an infrared light band is modulated using the reflection-type modulator so as to extract distance information, there is no light loss in the beam splitter 100. Thus, when the beam splitter 100 is employed in a 3D image acquisition apparatus including a 3D camera, a sufficient amount of light may be secured by minimizing light loss, so that more accurate distance information may be obtained. Also, only one object lens is needed, thus enabling the simultaneous capture of a color image and a depth image without a mismatch therebetween, and providing a compact 3D image acquisition apparatus.

Figure 6:
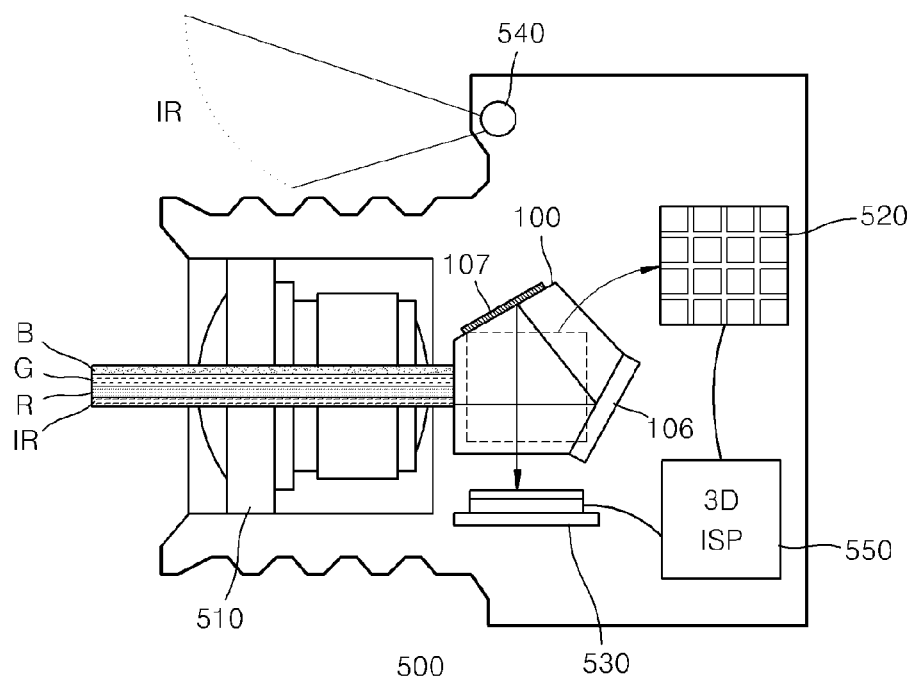
FIG. 6 is a schematic diagram of a structure of a 3D image acquisition apparatus employing the beam splitter of FIG. 1, according to an embodiment.

FIG. 6 is a schematic diagram of a 3D image acquisition apparatus 500 employing the beam splitter 100, according to an embodiment. Referring to FIG. 6, the 3D image acquisition apparatus 500 may include an infrared light source 540 for irradiating IR light onto an object, an objective lens 510 for focusing visible RGB light and IR light that are reflected from the object, the beam splitter 100 for dividing the visible RGB light from the IR light onto different paths, a first image sensor 520 for generating an image with respect to the visible RGB light (e.g., a color image), a second image sensor 530 for generating an image with respect to the IR light (e.g., a depth image), and a 3D image signal processor (ISP) 550 for generating a 3D image having depth information by using the images generated by the first and second image sensors 520 and 530.

The infrared light source 540 may generate a near IR ray having a wavelength of about 850 nm. The near IR ray generated by the infrared light source 540 may be irradiated to a target object (not shown). Afterward, the visible RGB light and the IR light that are reflected from the target object may be focused by the objective lens 510 that may be formed of a plurality of lens groups. The visible RGB light and the IR light that are focused by the objective lens 510 may be incident on the same light incident surface of the beam splitter 100. According to the aforementioned principles, the beam splitter 100 may split the visible RGB light from the IR light, such that the RGB light and the IR light exit through different light exit surfaces, respectively. In this way, the visible RGB light may be provided to the first image sensor 520, and the IR light may be provided to the second image sensor 530. The 3D ISP 550 may receive image signals from the first and second image sensors 520 and 530, and then may generate a 3D image having depth information by performing well-known signal processing processes.

The first image sensor 520 and the second image sensor 530 may be positioned at distances equivalent to the focal length of the objective lens 510. For example, the first image sensor 520 may be disposed facing the first light exit surface 111 (denoted as a dashed line box in FIG. 6) of the beam splitter 100, and the second image sensor 530 may be disposed facing the second light exit surface 114 of the beam splitter 100. It may be possible to appropriately adjust a focal length of the objective lens 510 and an optical path distance within the beam splitter 100 so that the first image sensor 520 may be directly disposed on the first light exit surface 111 of the beam splitter 100. Similarly, the second image sensor 530 may be directly disposed on the second light exit surface 114 of the beam splitter 100. However, due to limitations in optical design, the focal length of the objective lens 510 may be short so that a focus may exist within the beam splitter 100. In this case, a relay lens may be further used so as to relay an intermediate image, which is formed on a focus position in the beam splitter 100, to the first and second image sensors 520 and 530. The relay lens may be arranged on a surface of the beam splitter 100 so as to make the structure of the 3D image acquisition apparatus 500 be compact.

Figure 7:
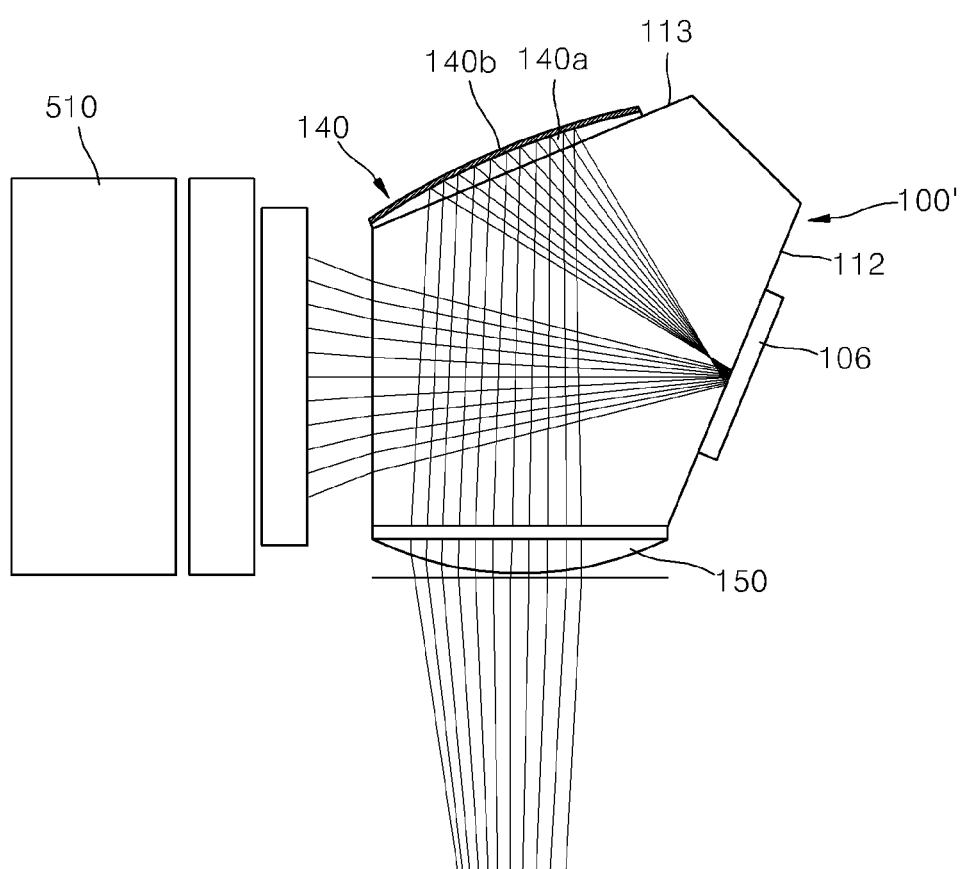
FIG. 7 is another diagram of the beam splitter of FIG. 1.

FIG. 7 is a schematic diagram of another aspect of the beam splitter 100 shown in FIG. 1, where FIG. 7 illustrates a beam splitter 100' having relay lenses formed on its surface is illustrated. Referring to FIG. 7, the beam splitter 100' may include a relay mirror 140 that is disposed on a surface of a second reflective surface 113, and a relay lens 150 that is disposed on a surface of a second light exit surface 114. In this case, a first reflective member 106 disposed on a first reflective surface 112 may be a reflection-type modulator. Alternatively, it is possible to dispose the relay mirror 140 on the first reflective surface 112 and to dispose a second reflective member 107 as the reflection-type modulator on the second reflective surface 113. The rest of the structure of the beam splitter 100' in FIG. 7 may be the same as that of the beam splitter 100 in FIG. 1.

The relay mirror 140 may be a concave mirror or a convex mirror according to the optical design of the system. In the case of FIG. 7, the relay mirror 140 is a concave mirror. In the case in which the relay mirror 140 is a concave mirror, as illustrated in FIG. 7, a convex light-transmitting material 140a is formed on the surface of the second reflective surface 113, and a reflective coating 140b is applied on an external surface of the convex light-transmitting material 140a, so that the relay mirror 140 is formed. In a case in which the relay mirror 140 is a convex mirror, a concave light-transmitting material is formed on the surface of the second reflective surface 113, and a reflective coating is applied on a surface of the concave light-transmitting material. Here, the light-transmitting material 140a may be separately fabricated and then may be applied to the second reflective surface 113, or may be integrally formed with the second reflective surface 113. Similarly, the relay lens 150 may separately fabricated and then may be applied to the second light exit surface 114, or may be integrally formed with the second light exit surface 114.

An object-side focus of a relay system including the relay mirror 140 and the relay lens 150 may be positioned at the location at which an intermediate image is formed within the beam splitter 100', and an image-side focus may be positioned on first or second image sensors 520 or 530. According to optical conditions, one of the relay mirror 140 and the relay lens 150 may be omitted.

Figure 8:
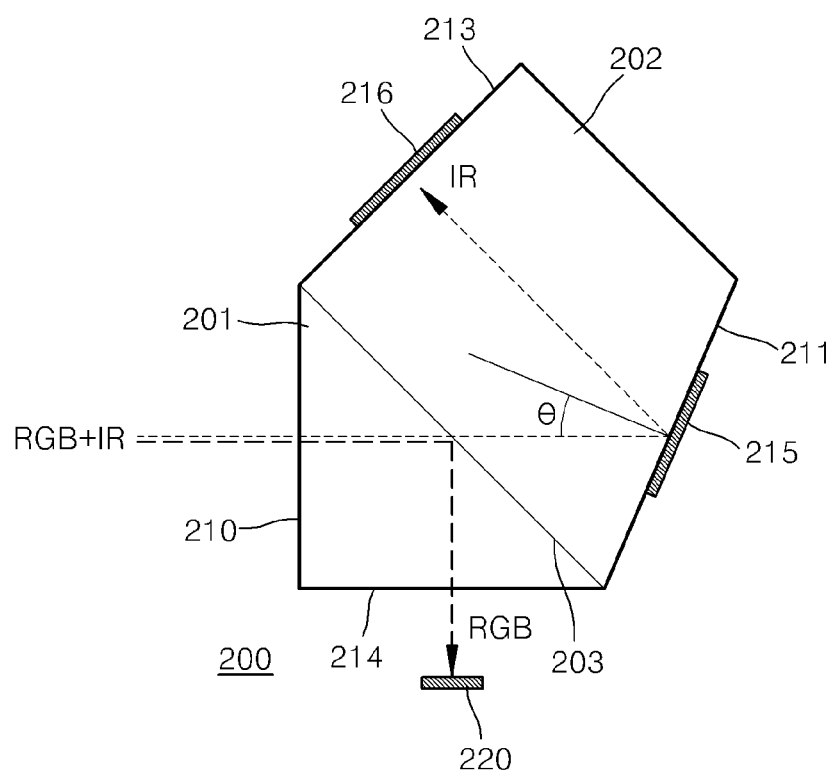
FIG. 8 is a cross-sectional view of a beam splitter according to another embodiment.

FIG. 8 is a cross-sectional view of a beam splitter 200 according to another embodiment. In the beam splitter 100 of FIG. 1, the beam splitting surface 104 is formed to be inclined between a front surface and a side surface of the beam splitter 100, so that the front surface of the beam splitter 100 functions as a common light incident surface 110 for RGB light and IR light, and the side surface functions as the first light exit surface 111 for the RGB light. Also, the second light exit surface 114 for the IR light is arranged at a bottom surface of the beam splitter 100. On the other hand, the beam splitter 200 of FIG. 8 is different from the beam splitter 100 of FIG. 1 in that an inclined beam splitting surface 203 is disposed between a front surface and a bottom surface of the beam splitter 200. Thus, in the beam splitter 200 of FIG. 8, the front surface functions as a common light incident surface 210 for RGB light and IR light, and the bottom surface functions as a first light exit surface 214 for the RGB light.

In more detail, the beam splitter 200 having a shape of a polyhedral prism, such as a pentaprism, may be formed by adhering an inclined surface of a polyhedral first part prism 201 having inclined surfaces to an inclined surface of a polyhedral second part prism 202 having inclined surfaces. A thin film coating (not shown), capable of reflecting or transmitting light according to the wavelength of the incident light, is applied on an interface between the first part prism 201 and the second part prism 202, so that the beam splitting surface 203 is formed. For example, the thin film coating may reflect RGB light having a relatively short wavelength and may transmit IR light having a relatively long wavelength. Thus, the RGB light and the IR light which enter the beam splitter 200 via the light incident surface 210 as the front surface, may be split by the beam splitting surface 203. For example, the RGB light is reflected from the beam splitting surface 203 and exits the beam splitter 200 via the first light exit surface 214 as the bottom surface. In this manner, the RGB light that exits the beam splitter 200 via the first light exit surface 214 may be directed to a dedicated image sensor 220 including a CCD. The image sensor 220 may be directly disposed on the first light exit surface 214.

As illustrated in FIG. 8, the light incident surface 210 and the first light exit surface 214 may be disposed at a front surface and a bottom surface of the first part prism 201, respectively, and may be adjacent to each other. Here, the light incident surface 210 may be perpendicular to an optical axis so as to allow incident light to be normal to the light incident surface 210. Thus, the incident light may enter the beam splitter 200 without being refracted by the light incident surface 210.

The IR light may pass through the beam splitting surface 203 and then may be incident on a reflective surface 211 that faces the light incident surface 210. For example, the reflective surface 211 may be disposed at a rear surface of the second part prism 202 of the beam splitter 200. Also, a reflective member 215 is disposed at a surface of the reflective surface 211 so as to reflect incident light. In the case of FIG. 8, the reflective member 215 may be a reflection-type modulator capable of modulating the incident IR light with a predetermined gain waveform and then reflecting it. The reflective surface 211 is inclined at a predetermined angle toward a second light exit surface 213 so as to prevent the IR light from being reflected back along a previous path. Thus, the IR light which is reflected from the reflective surface 211, travels to the second light exit surface 213.

However, as described above, when an inclination angle of the reflective surface 211 is too great, distortion may occur in light that is modulated and reflected by the reflection-type modulator. Thus, the reflective surface 211 may be arranged such that an angle (A) between an optical axis of the incident IR light and a line normal to the reflective surface 211 is within about 45 degrees. However, when the optical axis of the incident IR light is parallel to a line normal to the reflective surface 211, the IR light is reflected along a previous path. Thus, the reflective surface 211 may be arranged such that the angle between the optical axis of the incident IR light and a line normal to the reflective surface 211 is greater than 0 degrees. For example, an incident angle (A) at which the IR light is incident on the reflection-type modulator may be greater than 0 degrees and less than about 45 degrees. The angle (A) may be about 22.5 degrees.

The IR light which is reflected from the reflective surface 211, may exit the beam splitter 200 via the second light exit surface 213 disposed on an inclined surface of the beam splitter 200. As illustrated in FIG. 8, the second light exit surface 213 may be disposed on an inclined top surface of the second part prism 202. Also, in order to allow the IR light to exit the beam splitter 200 without being refracted by the second light exit surface 213, the second light exit surface 213 may be perpendicular to a travel direction of the IR light which has been reflected from the reflective surface 211. The IR light which exits the beam splitter 200 via the second light exit surface 213, may be directed to a dedicated image sensor 216 including a CCD. The image sensor 216 may be directly disposed on the second light exit surface 213.

Figure 9:
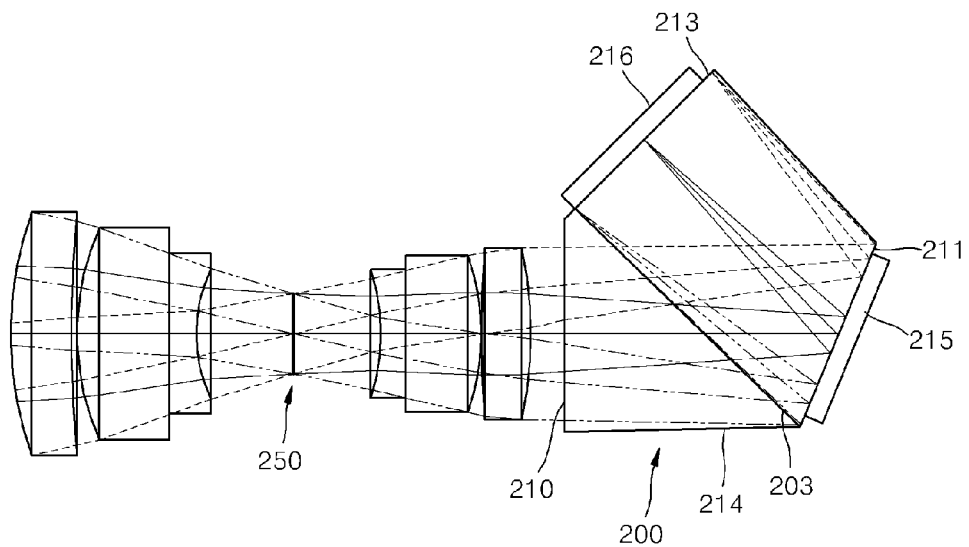
FIG. 9 illustrates an optical path of light in an infrared light band in the beam splitter of FIG. 8.

FIG. 9 illustrates an optical path of IR light which is focused on the image sensor 216 via the beam splitter 200 by using an objective lens 250, when the image sensor 216 is directly disposed on the second light exit surface 213. Referring to FIG. 9, the IR light which is focused by the objective lens 250 may enter the beam splitter 200 via the light incident surface 210 of the beam splitter 200. Afterward, the IR light is modulated and reflected by the reflective member 215 that is disposed as a reflection-type modulator on the reflective surface 211, and then the IR light is incident on the image sensor 216 via the second light exit surface 213. As illustrated in FIG. 9, the image sensor 216 is located at a focal point of the objective lens 250.

As described above, unlike the beam splitter 100 of FIG. 1 having the first and second reflective surfaces 112 and 113, the beam splitter 200 of FIG. 8 has only one reflective surface 211. Also, in the beam splitter 200 of FIG. 8, the second light exit surface 213, through which the IR light exits, is disposed only in the second part prism 202. On the other hand, in the beam splitter 100 of FIG. 1, the second light exit surface 114 is jointly formed by the bottom surface of the first part prism 102 and the bottom surface of the second part prism 103. While the beam splitter 100 of FIG. 1 has the second reflective surface 113 that is jointly formed by the top surface of the first part prism 102 and the top surface of the second part prism 103, the beam splitter 200 of FIG. 8 does not have a reflective surface that is jointly formed by the two part prisms, namely, the first and second part prisms 201 and 202.

Figure 10:
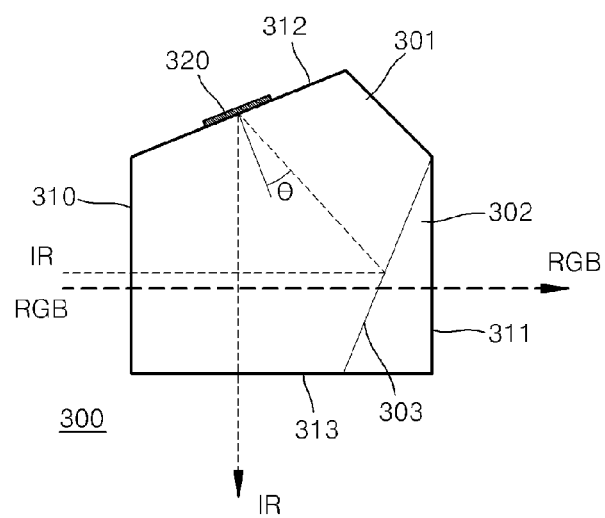
FIG. 10 is a cross-sectional view of a beam splitter according to another embodiment.

FIG. 10 is a cross-sectional view of a beam splitter 300 according to another embodiment. The beam splitter 300 of FIG. 10 may be formed by adhering an inclined rear surface of a first part prism 301, which has a shape of a polyhedral prism, such as a pentaprism, to a second part prism 302 having a right triangle shape. A thin film coating (not shown) capable of reflecting or transmitting light according to wavelengths is applied on an interface between the first part prism 301 and the second part prism 302, so that a beam splitting surface 303 is formed. For example, the thin film coating may transmit RGB light having a relatively short wavelength and may reflect IR light having a relatively long wavelength.

Referring to FIG. 10, a common light incident surface 310 for RGB light and IR light is disposed on a front surface of the first part prism 301. The RGB light and the IR light that enter the beam splitter 300 via the light incident surface 310 may be split by the beam splitting surface 303. For example, the RGB light passes through the beam splitting surface 303 and then exits the beam splitter 300 via a first light exit surface 311 disposed on a rear surface of the second part prism 302. The RGB light that exits the beam splitter 300 via the first light exit surface 311 may be directed to a dedicated image sensor (not shown) including a CCD. Thus, in the beam splitter 300 of FIG. 10, the light incident surface 310 may be disposed on the front surface of the first part prism 301, and the first light exit surface 311 may be disposed on the rear surface of the second part prism 302. The light incident surface 310 may be perpendicular to an optical axis so as to allow incident light to be normal to the light incident surface 310. Thus, the incident light may enter the beam splitter 300 without being refracted by the light incident surface 310.

The IR light may be reflected by the beam splitting surface 303 and then may be incident on a reflective surface 312 that is on an inclined top surface of the first part prism 301. For this, the beam splitting surface 303 may be inclined toward the reflective surface 312. A reflective member 320 is disposed on a surface of the reflective surface 312 so as to reflect incident light. In the case of FIG. 10, the reflective member 320 may be a reflection-type modulator capable of modulating the incident IR light with a predetermined gain waveform and then reflecting it. The reflective surface 312 is inclined at a predetermined angle toward a second light exit surface 313 so as to prevent the IR light from being reflected back along a previous path. Thus, the IR light which is reflected from the reflective surface 312, travels to the second light exit surface 313.

However, as described above, when an inclination angle of the reflective surface 312 is too great, distortion may occur in light that is modulated and reflected by the reflection-type modulator. Thus, the reflective surface 312 may be arranged such that an angle (A) between an optical axis of the incident IR light and a line normal to the reflective surface 312 is within about 45 degrees. However, when the optical axis of the incident IR light is parallel to the line normal to the reflective surface 312, the IR light is reflected back along a previous path. Thus, the reflective surface 312 may be arranged such that the angle between the optical axis of the incident IR light and the line normal to the reflective surface 312 is greater than 0 degrees. For example, an incident angle (A) at which the IR light is incident on the reflection-type modulator may be greater than 0 degrees and less than about 45 degrees. The angle (A) may be about 22.5 degrees.

The IR light which is reflected from the reflective surface 312, may exit the beam splitter 300 via the second light exit surface 313 disposed on a bottom surface of the beam splitter 300. As illustrated in FIG. 10, the second light exit surface 313 may be disposed on a bottom surface of the first part prism 301. While the bottom surface of the beam splitter 300 is jointly formed by the bottom surface of the first part prism 301 and a bottom surface of the second part prism 302, the reflected IR light may exit the beam splitter 300 only via the portion of second light exit surface 313 disposed on the bottom surface of the first part prism 301. In order to allow the IR light to exit the beam splitter 300 without being refracted by the second light exit surface 313, the second light exit surface 313 may be perpendicular to a travel direction of the IR light which has been reflected from the reflective surface 312. The IR light that exits the beam splitter 300 via the second light exit surface 313 may be directed to a dedicated image sensor (not shown) including a CCD.

Similarly to the beam splitter 100 of FIG. 1, the aforementioned beam splitters 200 and 300 of FIGS. 8 and 10, respectively, may also be employed in the 3D image acquisition apparatus 500 of FIG. 6.

In the description above, a beam splitter for a 3D camera, and a 3D image acquisition apparatus employing a beam splitter according to the one or more of the above embodiments are described.

It should be understood that the exemplary embodiments described herein should be considered in a descriptive sense only and not for purposes of limitation. Descriptions of features or aspects within each embodiment should be considered as available for other similar features or aspects in other embodiments.

What is claimed is:

1. A beam splitter comprising:
a light incident surface;
a beam splitting surface which is disposed in the beam splitter and inclined with respect to the light incident surface, wherein the beam splitting surface is configured to reflect substantially all of the light having a first wavelength of light incident thereon and transmit substantially all of the light having a second wavelength incident thereon through the beam splitting surface, wherein the second wavelength is different from the first wavelength;
a first light exit surface which is oriented such that the light having the first wavelength that is reflected from the beam splitting surface exits the beam splitter through the first light exit surface;
a first reflective surface which is oriented to reflect the light having the second wavelength that has been transmitted through the beam splitting surface;
a second reflective surface which is oriented to reflect the light having the second wavelength that has been reflected from the first reflective surface; and
a second light exit surface which is oriented such that the light having the second wavelength that has been reflected from the second reflective surface exits the beam splitter through the second light exit surface.

2. The beam splitter of claim 1, wherein:
the first light exit surface is substantially perpendicular to an optical axis of light incident thereon, and
the second light exit surface is substantially perpendicular to an optical axis of light incident thereon.

3. The beam splitter of claim 1, wherein the second light exit surface is adjacent to the light incident surface, the first light exit surface, and the first reflective surface and the second light exit surface faces the second reflective surface.

4. The beam splitter of claim 1, further comprising a first reflective member disposed on the first reflective surface, and a second reflective member disposed on the second reflective surface.

5. The beam splitter of claim 4, wherein a reflection-type modulator which modulates and reflects the light having the second wavelength is disposed on one of the first reflective member and the second reflective member, and the other one of the first reflective member and the second reflective member comprises a reflective mirror.

6. The beam splitter of claim 5, wherein the first reflective surface is inclined toward the second reflective surface, and the second reflective surface is inclined toward the second light exit surface.

7. The beam splitter of claim 6, wherein the one of the first reflective surface and the second reflective surface on which the reflection-type modulator is disposed is inclined, wherein an angle between an optical axis of the light having the second wavelength incident on the reflection-type modulator and a line normal to the reflection-type modulator is greater than 0 degrees and less than about 45 degrees.

8. The beam splitter of claim 7, wherein the angle between the optical axis of the light having the second wavelength incident on the reflection-type modulator and the line normal to the reflection-type modulator is about 22.5 degrees.

9. The beam splitter of claim 1, wherein the beam splitter further comprises a first part prism, that is a polyhedral prism, adhered to a second part prism, that is a polyhedral prism.

10. The beam splitter of claim 9, wherein the beam splitting surface comprises a thin film coating formed on an interface between the first part prism and the second part prism.

11. The beam splitter of claim 9, wherein the light incident surface is a front surface of the first part prism, and the first light exit surface is a side surface of the first part prism, and the light incident surface and the first light exit surface are adjacent to each other.

12. The beam splitter of claim 9, wherein the first reflective surface is a rear surface of the second part prism and faces the light incident surface.

13. The beam splitter of claim 9, wherein the second reflective surface is jointly formed by an inclined top surface of the first part prism and an inclined top surface of the second part prism, and the second light exit surface is jointly formed by a bottom surface of the first part prism and a bottom surface of the second part prism.

14. The beam splitter of claim 1, further comprising a relay lens disposed on the second light exit surface.

15. The beam splitter of claim 1, further comprising a relay mirror disposed on one of the first reflective surface and the second reflective surface.

16. A three-dimensional (3D) image acquisition apparatus comprising:
an infrared light source which irradiates infrared light to an object;
an objective lens which focuses visible light and infrared light that are reflected from the object;

the beam splitter of claim 1, wherein the light having the first wavelength is visible light and the light having the second wavelength is infrared light;
a first image sensor which is disposed to receive visible light from the first light exit surface and which generates an image with respect to the visible light;
a second image sensor which is disposed to receive infrared light from the second light exit surface and which generates an image with respect to the infrared light; and
a 3D image signal processor which generates a 3D image having depth information by using the images generated by the first and second image sensors.

17. The 3D image acquisition apparatus of claim 16, wherein the first image sensor faces the first light exit surface of the beam splitter, and the second image sensor faces the second light exit surface of the beam splitter.

18. The 3D image acquisition apparatus of claim 17, wherein the first image sensor is disposed on the first light exit surface of the beam splitter, and the second image sensor is disposed on the second light exit surface of the beam splitter.

19. A beam splitter, wherein the beam splitter has a cross-sectional shape which is a pentagon, the beam splitter comprising:
a first part prism adhered to a second part prism such that an inclined beam splitting surface, which is disposed in the beam splitter, comprises an interface between the first part prism and the second part prism;
wherein the first part prism comprises a light incident surface and, of light incident on the beam splitting surface from the light incident surface, reflects substantially all light having a first wavelength of light incident thereon, and transmits substantially all light having a second wavelength incident thereon, different from the first wavelength, through the beam splitting surface;
wherein the first part prism further comprises a first light exit surface through which the light having the first wavelength that has been reflected by the beam splitting surface exits the beam splitter;
wherein the second part prism comprises:
a first reflection surface which reflects the light having the second wavelength that has been transmitted through the beam splitting surface;
a second reflection surface which reflects the light having the second wavelength that has been reflected by the first reflection surface;
a second light exit surface through which the light having the second wavelength that has been reflected by the second reflection surface exits the beam splitter; and
a reflection type modulator disposed on one of the first reflection surface and the second reflection surface, which modulates and reflects the light having the second wavelength.

20. A three-dimensional (3D) image acquisition apparatus comprising:
a light source which irradiates an object with infrared light;
an objective lens which transmits visible light and infrared light reflected from the object;
a beam splitter having a cross-sectional shape which is a pentagon, the beam splitter comprising:
a first part prism adhered to a second part prism such that an inclined beam splitting surface, which is disposed in the beam splitter, comprises an interface between the first part prism and the second part prism;
wherein the first part prism comprises a light incident surface oriented to receive the visible light and the infrared light transmitted by the objective lens,
wherein, of light incident on the beam splitting surface from the light incident surface, the beam splitting surface reflects substantially all visible light having a first wavelength from light incident thereon and transmits substantially all infrared light having a second wavelength incident thereon through the beam splitting surface;
wherein the first part prism further comprises a first light exit surface through which the visible light exits the beam splitter;
wherein the second part prism comprises:
a first reflection surface which reflects the infrared light that has been transmitted through the beam splitting surface;
a second reflection surface which reflects the infrared light that has been reflected by the first reflection surface;
a second light exit surface through which the infrared light that has been reflected by the second reflection surface exits the beam splitter; and
a reflection type modulator disposed on one of the first reflection surface and the second reflection surface, which modulates and reflects the infrared light;
a first image sensor which receives the visible light transmitted through the first exit surface and which generates an image with respect to the visible light;
a second image sensor which receives the infrared light transmitted through the second exit surface and which generates an image with respect to the infrared light; and
a 3D image signal processor which generates a 3D image based on the images generated by the first and second image sensors.

21. The beam splitter of claim 1, wherein the filtering of the beam splitting surface is performed by a thin film coating.

* * * * *